US008628534B2

(12) United States Patent
Jones et al.

(10) Patent No.: US 8,628,534 B2
(45) Date of Patent: Jan. 14, 2014

(54) ULTRASONIC CUTTING DEVICE (75) Inventors: Bryan S. Jones, Quincy, MA (US);
Christopher Ramsay, West Wareham, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 1069 days.

(21) Appl. No.: 11/050,265

(22) Filed: Feb. 2, 2005

(65) Prior Publication Data
US 2006/0195107 A1    Aug. 31, 2006

(51) Int. Cl.
*A61B 17/00* (2006.01)
*A61B 17/32* (2006.01)

(52) U.S. Cl.
USPC ............................................. 606/79; 606/169

(58) Field of Classification Search
USPC .............. 606/79–85, 169–172, 166; 433/119, 433/122, 169, 166; 604/22, 164.06
See application file for complete search history.

(56) References Cited

U.S. PATENT DOCUMENTS

| | | |
|---|---|---|
| 4,021,920 A | 5/1977 | Kirschner et al. |
| 5,019,083 A | 5/1991 | Klapper et al. |
| 5,382,251 A | 1/1995 | Hood et al. |
| 5,593,416 A | 1/1997 | Donahue |
| 5,630,420 A | 5/1997 | Vaitekunas |
| 5,792,044 A | 8/1998 | Foley et al. |
| 5,873,873 A | 2/1999 | Smith et al. |
| 5,893,835 A | 4/1999 | Witt et al. |
| 5,935,144 A | 8/1999 | Estabrook |
| 5,938,633 A * | 8/1999 | Beaupre ........................... 604/22 |
| 5,944,737 A | 8/1999 | Tsonton et al. |
| 5,947,984 A | 9/1999 | Whipple |
| 5,954,736 A | 9/1999 | Bishop et al. |
| 5,957,943 A | 9/1999 | Vaitekunas |
| 5,980,510 A | 11/1999 | Tsonton et al. |
| 5,989,264 A | 11/1999 | Wright |
| 6,004,335 A | 12/1999 | Vaitekunas et al. |
| 6,068,647 A | 5/2000 | Witt et al. |
| 6,074,389 A * | 6/2000 | Levine et al. ................... 606/45 |
| 6,090,120 A | 7/2000 | Wright et al. |
| 6,206,844 B1 | 3/2001 | Reichel et al. |

(Continued)

FOREIGN PATENT DOCUMENTS

EP    0482195 A1    4/1992
JP    62-142544    6/1987

(Continued)

OTHER PUBLICATIONS

International Search Report for Application No. PCT/US06/03616, dated Jun. 12, 2006.

(Continued)

*Primary Examiner* — Gary Jackson
*Assistant Examiner* — Richard Louis
(74) *Attorney, Agent, or Firm* — Nelson Mullins Riley & Scarborough LLP (57) ABSTRACT

An ultrasonic surgical cutting method and apparatus is provided wherein the method and apparatus allows for the cutting of bone from within a hollow pathway such that a cutter associated with the ultrasonic method and apparatus remains sufficiently cool to prevent necrosis of the bone being cut. Furthermore the ultrasonic device and method can be employed in the cutting of soft tissue, wherein a cooled cutter is used to prevent the sticking of soft tissue to the cutting blade of the device during use.

11 Claims, 7 Drawing Sheets

(56) References Cited

U.S. PATENT DOCUMENTS

| | | | |
|---|---|---|---|
| 6,251,110 B1 | 6/2001 | Wampler | |
| 6,257,241 B1 | 7/2001 | Wampler | |
| 6,274,963 B1 | 8/2001 | Estabrook et al. | |
| 6,287,344 B1 | 9/2001 | Wampler et al. | |
| 6,325,811 B1 | 12/2001 | Messerly | |
| 6,352,532 B1 | 3/2002 | Kramer et al. | |
| 6,358,254 B1 | 3/2002 | Anderson | |
| 6,379,371 B1 * | 4/2002 | Novak et al. | 606/169 |
| 6,416,486 B1 | 7/2002 | Wampler | |
| 6,425,906 B1 | 7/2002 | Young et al. | |
| 6,432,118 B1 | 8/2002 | Messerly | |
| 6,440,138 B1 * | 8/2002 | Reiley et al. | 606/79 |
| 6,454,781 B1 | 9/2002 | Witt et al. | |
| 6,458,142 B1 | 10/2002 | Faller et al. | |
| 6,497,715 B2 | 12/2002 | Satou | |
| 6,558,386 B1 * | 5/2003 | Cragg | 606/61 |
| 6,561,983 B2 | 5/2003 | Cronin et al. | |
| 6,663,641 B1 | 12/2003 | Kovac et al. | |
| 6,679,899 B2 | 1/2004 | Wiener et al. | |
| 6,695,847 B2 | 2/2004 | Bianchetti et al. | |
| 6,746,451 B2 | 6/2004 | Middleton et al. | |
| 6,958,071 B2 | 10/2005 | Carusillo et al. | |
| 2001/0004695 A1 | 6/2001 | Vercellotti et al. | |
| 2002/0156530 A1 * | 10/2002 | Lambrecht et al. | 623/17.16 |
| 2003/0004517 A1 * | 1/2003 | Anderson | 606/90 |
| 2003/0191474 A1 | 10/2003 | Cragg et al. | |
| 2003/0212400 A1 | 11/2003 | Bloemer et al. | |
| 2004/0133201 A1 * | 7/2004 | Shluzas et al. | 606/61 |
| 2004/0147934 A1 * | 7/2004 | Kiester | 606/80 |
| 2005/0065530 A1 | 3/2005 | Stauch et al. | |
| 2005/0119612 A1 | 6/2005 | Delval et al. | |
| 2005/0131439 A1 | 6/2005 | Brett | |

FOREIGN PATENT DOCUMENTS

| | | |
|---|---|---|
| JP | 10-5237 | 1/1998 |
| JP | 2002-510517 | 4/2002 |
| JP | 2004-512855 | 4/2004 |
| WO | 91/17716 A1 | 11/1991 |
| WO | 99/51149 | 10/1999 |
| WO | 99/51149 A1 | 10/1999 |
| WO | 01/60268 | 8/2001 |
| WO | 02/21994 A2 | 3/2002 |

OTHER PUBLICATIONS

Supplementary European Search Report for Application No. 06720112.9, dated Jan. 5, 2010.
Japanese Office Action Application No. 2007-554198, dated Apr. 19, 2011.
European Communication for Application No. 06720112.9, dated Jul. 8, 2010.
Japanese Office Action for Application No. 2007-554198, dated Oct. 4, 2011.
Australian Office Action for Application No. 2006210796, dated Sep. 13, 2010.
European Office Action for Application No. EP06720112.9, dated Dec. 13, 2011.
Japanese Office Action for Application No. 2007-554198, 5 pages, dated Feb. 14, 2012.
Canadian Office Action for Application No. 2,596,651, 2 pages, dated Aug. 17, 2012.
Canadian Office Action for Application No. 2,596,651, 3 pages, dated May 15, 2013.
Japanese Written Interrogation for Application No. 2007-554198, 7 pages, dated Oct. 23, 2012.

* cited by examiner

ULTRASONIC CUTTING DEVICE

RELATED APPLICATIONS

The present invention relates to U.S. patent application Ser. No. 11/050,158 entitled "Ultrasonic Cutting Device", filed on Feb. 2, 2005.

FIELD OF THE INVENTION

The present invention relates to an ultrasonic cutting device, and more particularly to a system and method for cutting bone using an ultrasonic cutting device while preventing heat damage to the bone and neighboring tissue.

BACKGROUND OF THE INVENTION

The use of ultrasonic medical devices in surgery is widely known in various surgical fields. Traditional surgical instruments using ultrasonic frequencies typically use the ultrasonic energy to dissect, coagulate, and cut living tissue during surgery. Existing ultrasonic surgical devices typically employ an ultrasonic transducer to translate electrical energy provided to the transducer into mechanical energy for use in the intended surgical procedure. The mechanical vibratory motion is typically delivered to a distal end of the surgical instrument where a cutter is located. Due to the mechanical vibratory motion, heat is generated at the cutter. In traditional medical procedures this heat is a sought after byproduct of the ultrasonic mechanical energy delivered to the cutter, as the heat aids in the coagulation of tissue that is cut by the surgical instrument.

The heated output of traditional ultrasonic surgical devices, however, does introduce several inherent problems when used in various forms of surgery. If these devices are used to attempt to cut bone, for example, the high concentrated heat and mechanical vibration can result in the temporary or permanent loss of blood supply to the region of bone in contact with the surgical device. This loss of blood supply in the bone is associated with necrosis of the bone, wherein bone tissue dies. Such death of bone tissue is not clinically desirable. In light of this, the use of ultrasonic cutting techniques with dense materials such as bone is not practical and is generally avoided. When faced with a need to cut bone, traditional invasive procedures are generally used. These invasive procedures generally require a larger incision and expose a patient to a greater risk of injury or infection. Furthermore, traditional mechanical means used to cut bone often employ vibrating or rotating instruments. Such instruments may not differentiate between bone and surrounding soft tissue, therefore the potential remains for unintentional damage to the surrounding soft tissue which may result in permanent injury to a patient.

Furthermore, existing bone cutting surgical devices use a combination of low frequency, located outside of the ultrasonic range, and low amplitude levels to slowly cut through bone. With such an approach, however a long period of time is required to cut through a region of bone. During a surgical procedure where the patient is under the effects of aesthesia, a surgeon generally wishes to minimize the time that the procedure takes to perform. While increasing the frequency or amplitude of a bone cutting device would decrease the time required to cut through the bone, such an increase of frequency or amplitude results in excessive heat generation at the cutter and the problems discussed above. Additionally, the high heat of the device results in cauterization of soft tissue which may result in irreversible damage to a patient.

SUMMARY OF INVENTION

In light of the inherent problems and concerns of existing surgical cutting techniques, a cooling mechanism attached to the cutter of an ultrasonic surgical device is beneficial. When the ultrasonic device is used to cut bone, reduction of heat at the cutter prevents bone necrosis. Additionally, as the cutter is operating at a less elevated temperature, damage to tissue surrounding the cutter is less of a concern. In light of this, should a cooled ultrasonic cutter stray from the intended subject and accidentally come into contact or close contact with an unintended region of tissue, the likelihood of damage to this tissue is reduced.

The present invention relates to surgical cutting devices wherein ultrasonic vibration can be used in conjunction with a cooling mechanism. Using a cutting and cooling arrangement, as provided in the present invention, a cooled cutter can be used in cutting hard tissues such as bone, and is further capable of preventing heat related damage to hard or soft tissue surrounding the site of intended use.

Providing an ultrasonic cutting device wherein the cutter is maintained at a reduced temperature offers numerous advantages as compared to existing surgical devices. Firstly, the combination of ultrasonic cutting frequencies provides for speedy removal of bone during a surgical procedure. Additionally, as the cutting tip is at a reduced operating temperature, traditional problems with bone necrosis due to heat are reduced. In light of this, damage to the region of hard or soft tissue surrounding the location of the cut are minimized.

Additionally, the inherent concerns of a surgeon when using a high-heat ultrasonic cutting device in close proximity to hard or soft tissue that is not being cut are further eliminated by a ultrasonic surgical device that maintains a reduced cutter temperature. For example, extensive necrosis to cortical bone has been reported at temperatures of 70° C. The temperature threshold where tissue damage occurs has been found to be 56° C. Some studies have correlated thermal damage to tissue to the magnitude of temperature and the period of time during which the tissue is subjected to damaging temperatures. This thermal damage has been shown to effect bone reformation. Heating bone to 47° C. or 50° C. for 1 minute can cause significantly reduced bone reformation. Furthermore, nervous tissue is particularly sensitive to elevated temperatures and may become damaged at temperature at 42° C. In light of this, the present invention provides a reduced heat cutting tip such that damage to hard of soft tissue in the region to be cut is prevented.

In one embodiment of the present invention, during a surgical procedure where bone is to be cut, should a surgeon accidentally stray from the intended target bone and come into contact with surrounding nervous tissue, a reduced temperature ultrasonic cutting device is less likely to cause damage to the nervous tissue. In light of this, unintended nerve damage and paralysis is subsequently avoided while using a reduced temperature ultrasonic cutting device.

The present invention can additionally perform lateral cutting operations. For example, using the present invention, a surgeon can laterally cut a region of bone from within a predefined hollow provided in the bone. For example, when used during spinal surgery, the present invention offers a surgeon the benefit of a compact ultrasonic device that can be readily guided down a predefined hollow pathway to a fixed depth. In one such surgical procedure, namely a stenosis correction procedure, the pedicles of a vertebrae are cut at corresponding points such that the pedicle can be separated from the main portion of the vertebral segment. Such a procedure is defined in U.S. patent application No. US 2003/0212400 to Bloemer, and U.S. Pat. No. 6,358,254 B1 to Anderson, both of which are herein incorporated by reference. In accordance with the Bloemer application and Anderson patent, a hollow pathway is provided in the pedicle region of a vertebra. This hollow pathway can be generated using existing drilling techniques. Following the drilling of a hollow pathway, a need exists to cut through the material of the pedicle region such that an expandable screw may be placed within the hollow pathway. The required cutting, if completed from within the predefined hollow region, must be lateral in nature. The present invention, and its lateral cutting aspects, allows for the predefined hollow in the bone to be used to properly orient the surgical instrument. This expandable screw, placed in the now severed pedicle, allows for the separation of the pedicle from the main portion of the vertebrae such that stenosis is eliminated.

Using the present invention, the pedicle region can be carefully cut at fixed locations in a lateral manner such that the expandable screw can later be implanted and expand. Such an arrangement eliminates the potential for error in cutting a region of a vertebra, as the predefined hollow is used to orient the cutter, and further provides a readily repeatable cut along various regions of a vertebra. Additionally, the present ultrasonic cutter is easily operable by a surgeon, requiring only a simple insertion and revolution of a hand piece assembly. In light of this, when used in conjunction with a predefined hollow pathway, spinal surgery can be performed in a minimally invasive manner such that repeatable results can be obtained without unintended damage to surrounding soft tissue. As the surgical procedure can be less invasive than traditional techniques, unnecessary trauma to a patient is prevented and the potential for infection is greatly reduced.

Additionally, when the device is employed using a high amplitude signal, soft tissue can be cut. As the present invention includes a cooled cutter, the cooled cutter arrangement is such that soft tissue cut by the present invention does not unnecessarily stick to the cutter.

BRIEF DESCRIPTION OF THE DRAWINGS

The present invention will become better understood with reference to the following description and accompanying drawings, wherein.

DETAILED DESCRIPTION

The present invention generally relates to an ultrasonic surgical cutting system, wherein a lateral cutter is used to cut through hard tissue such as bone, while simultaneously preventing unintended damage to tissue adjacent to the intended tissue to be cut. Additionally, the present invention provides for cutting of an intended material using a lateral cutter, wherein the lateral cutter has a reduced temperature. Because the device employs a cooled cutter arrangement, inherent problems of ultrasonic cutting instruments are reduced. For example, using a cooled cutter arrangement coupled with a low initial amplitude, bone may be cut in a manner such that necrosis does not develop. Additionally, while cutting a hard tissue such as bone, should the cooled cutter contact surrounding soft tissue, damage to the soft tissue will not result. Furthermore, coupled with an increase in amplitude to cut soft tissue, the cutter's temperature is reduced so that soft tissue cut by the present invention does not unnecessarily stick to the cutter.

Figure 1:
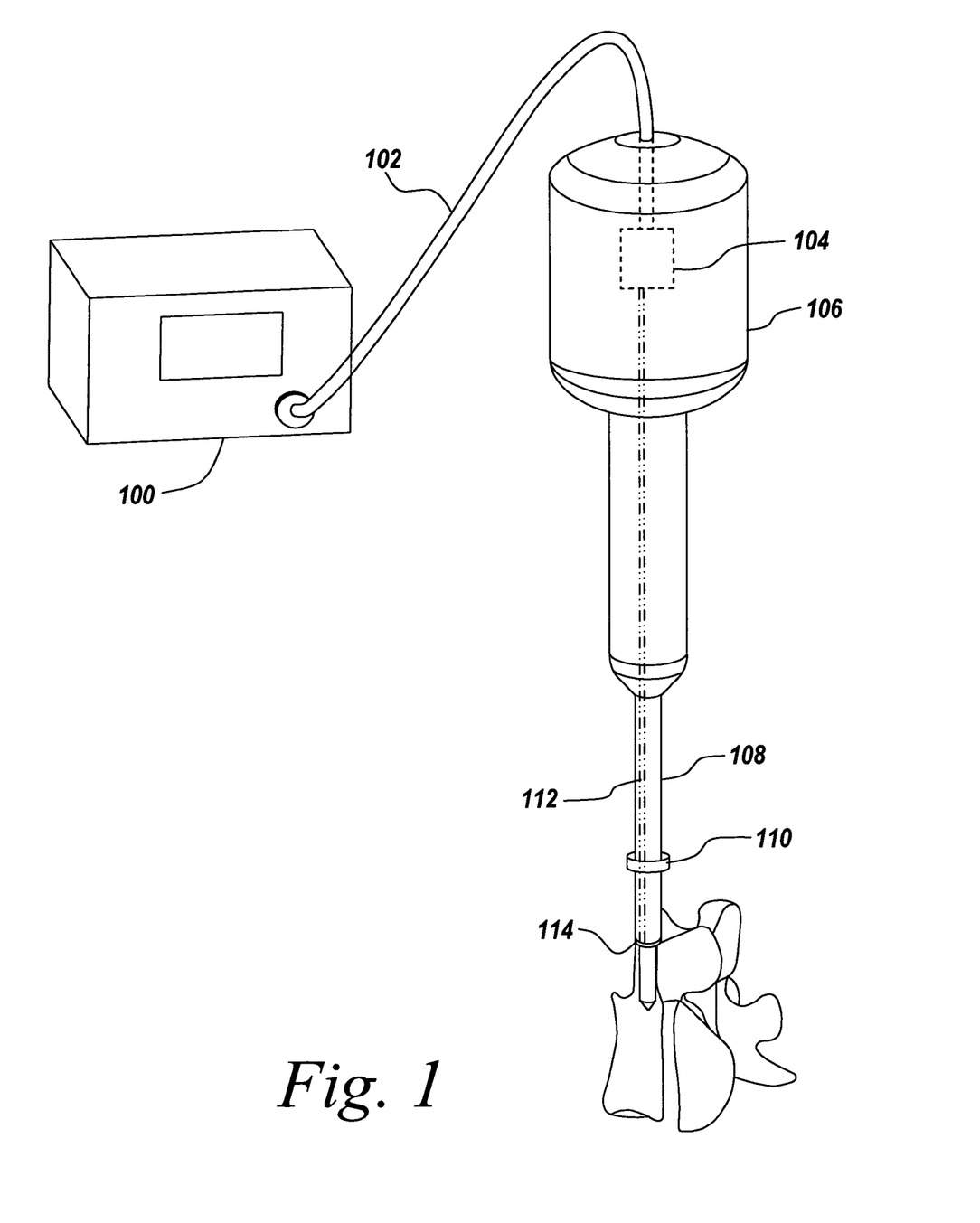
FIG. 1 is a is an illustrative graphical embodiment of a system for use with the present invention in accordance with one aspect of the present invention.

FIG. 1 is a is an illustrative graphical embodiment of a system for use with the present invention in accordance with one aspect of the present invention. The present system includes an ultrasonic generator 100 capable of producing an ultrasonic frequency. The generator's frequency is in the range of about 22 Khz to 45 Khz and contains a variable amplitude component. For example, a low amplitude can be employed while cutting a hard tissue such as bone, and a higher amplitude can be employed when the intended tissue to be cut is soft. Associated with the generator 100 is an ultrasonic transducer 104. The ultrasonic transducer allows for the conversion of electrical energy supplied by the ultrasonic generator 100 into mechanical energy which can be transmitted to a vibratory shaft 112 associated with the transducer 104. The transfer of energy between the ultrasonic generator 100 and the transducer 104 occurs using a electrical pathway 102. The electrical pathway can be a electrical connector between signal generator 100 and transducer 104 such that electrical energy can be delivered to the transducer 104. In the alternative, the electrical pathway 102 can be eliminated and the remotely located ultrasonic generator 100 can be integrated directly into the surgical cutting system. The coupling between the transducer 104 and the vibratory shaft 112 is such that mechanical motion generated by the transducer 104 is transferred directly to the vibratory shaft 112. The vibratory shaft 112 is therefore sized and constructed of an appropriate material to sufficiently transmit the mechanical motion of the transducer 104 without unnecessary attenuation of the ultrasonic signal. For example, surgical grade stainless steel or titanium may be used in construction of the vibratory shaft 112. The ultrasonic generator 100, transducer 104 and electrical pathway 102 may take numerous forms as understood by one skilled in the art. For example, existing commercially available surgical instruments including the aforementioned elements may be used in practicing the present invention. Furthermore, the need for the vibratory shaft 112 may be reduced or eliminated based upon shape and orientation of the transducer 104 employed.

The vibratory shaft 112 is contained within a guide tube 108. The guide tube 108 is sized such that the guide tube 108 can be readily placed down a predefined hollow pathway (not shown) such that the hollow pathway serves to orient the guide tube 108 and associated ultrasonic surgical cutting system. Furthermore the guide tube serves to contain the vibratory shaft 112 such that the vibratory shaft does not come in contact with surrounding tissue or bone. The predefined hollow pathway can be readily provided using existing techniques such as drilling. For example, during use in stenosis correction surgery, a hollow pathway can be provided in each pedicle of a vertebra such that upon cutting the pedicle an anterior and posterior region is formed. Using a mechanical means, these anterior and posterior regions may be separated such that nervous tissue compression within the vertebrae is eliminated.

Associated with the distal end of the vibratory shaft 112 is a cutter 114. In the present embodiment, the cutter illustrated is a lateral cutter located perpendicular to the vibratory shaft 112. One skilled in the art, however, will readily recognize that the cutter may be placed at a variety of angles in relation to the vibrator shaft 112 such that the circumferential cut traced by the cutter 114 is at the required angle specific to the surgical procedure to be performed. The cutter 144 is sized and oriented such that while in the stored position the footprint of the cutter remains within the region defied by the guide tube. The cutter can be formed of any biocompatible material such as titanium or surgical grade stainless steel, and may be of various thicknesses. In one embodiment of the present invention, when used in stenosis correction the cutter is in the range of 2 to 3 millimeters thick. One skilled in the art will readily recognize, however, that the cutter thickness can be readily varied based upon the surgical needs of the intended procedure. The guide tube may be inserted into the hollow pathway such that the cutter 114 does not contact the walls of the hollow pathway during insertion. For illustrative purposes, the cutter 114 is shown as permanently affixed to the vibratory shaft 112. One skilled in the art will readily recognize that the cutter 114 may be affixed to the vibratory shaft 112 using various arrangements such as mechanical fastening means like screws. In the alternative, the distal end of the vibratory shaft 112 may contain a threaded section, such that an intended cutter 114 can simply be threaded onto the ultrasonic cutting system based upon the pending surgical procedure. Using such an arrangement, a surgeon can use the present invention during a plurality of surgical procedures which require specialized cutters 114 for use in the cutting of bone.

In conjunction with the insertion of the guide tube 108 into the hollow pathway, an adjustable stop 110 located on the guide tube 108 can be utilized in defining the depth of penetration of the guide tube 108 within the hollow pathway. The adjustable stop 110 can be preconfigured by a surgeon prior to insertion of the guide tube 108 into a hollow pathway. In one embodiment of the present invention, a set of calibration markings can be located along the length of the guide tube 108 such that a distance from cutter 114 to adjustable stop 110 can be easily set. In light of this, repeatable cuts at a fixed depth can be readily performed. When used in connection with stenosis correction surgery, for example, the depth of cut in both regions of the pedicle can be easily maintained using the adjustable stop 110. The adjustable stop 110 can be fixed using several means as understood by one skilled in the art. For example, a simple set screw arrangement can be employed wherein a surgeon can use a supplied tool to lock the adjustable stop in place on the guide tube 108. In the alternative, the adjustable stop 110 can simply be retained along the length of the guide tube 108 using a friction fit.

Figure 2A:
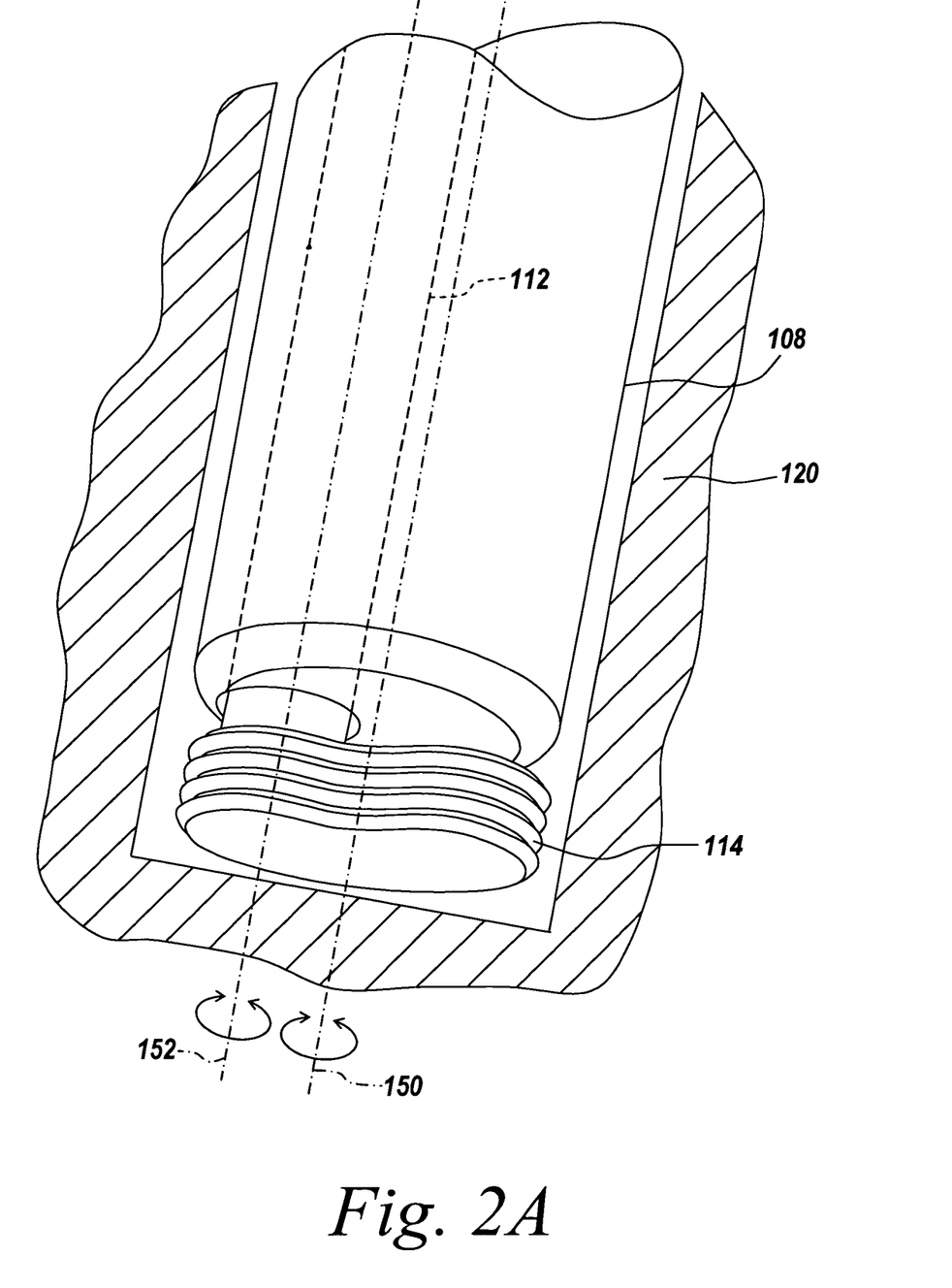
FIG. 2A is an illustrative embodiment of the present invention in a state where the cutter is retracted while located in a predefined hollow.
Figure 2B:
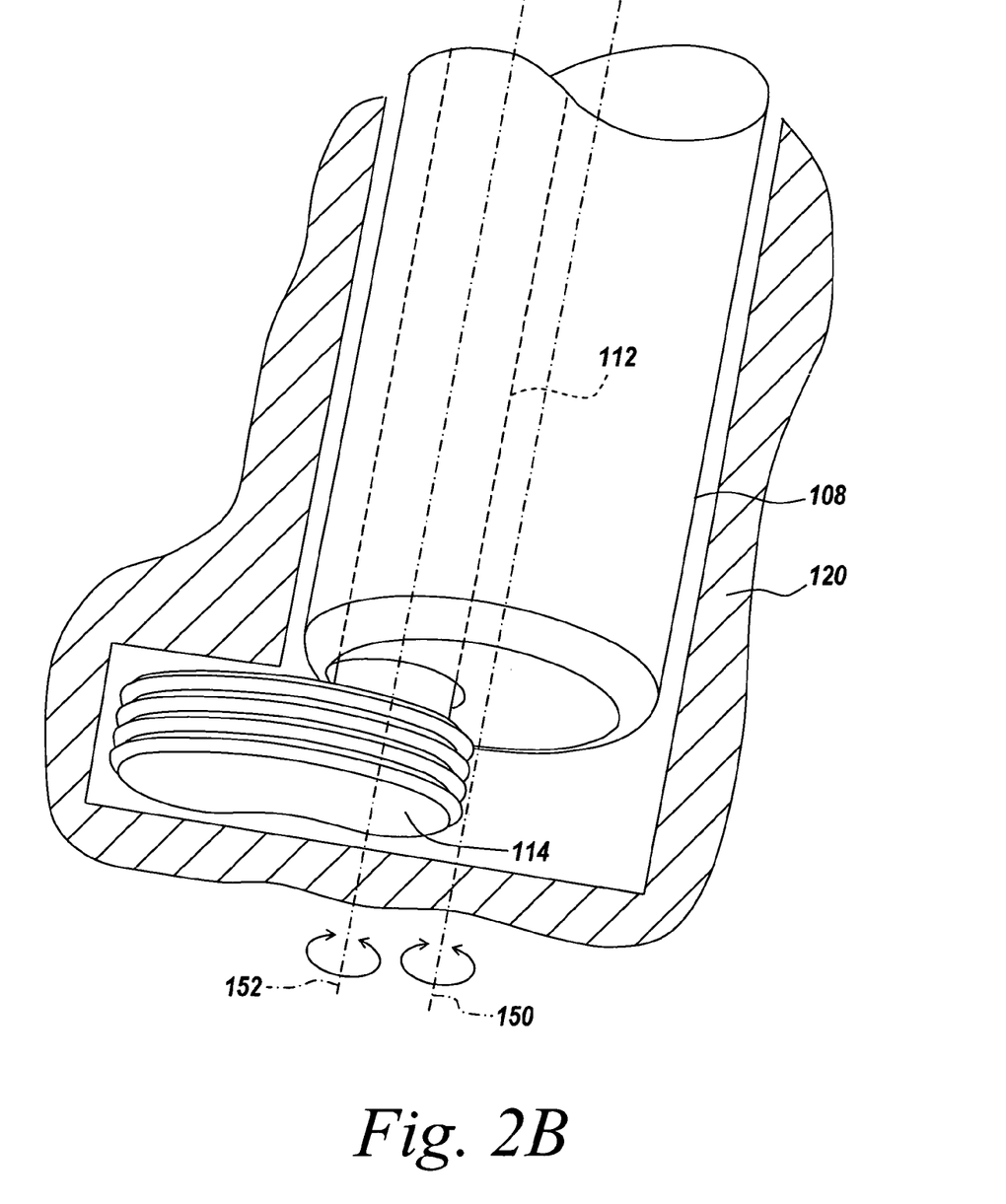
FIG. 2B is an illustrative embodiment of the present invention in a state where the cutter is extended while located in a predefined hollow.

The vibratory shaft 112 of the present invention is located in an offset manner to the centerline of the guide tube 108 such that the cutter 114 is located within the periphery of the guide tube while stored in the retracted portion. FIG. 2A illustrates a retracted view of the cutter 114 prior to deployment of the cutter. FIG. 2A further illustrates the eccentrically mounted vibratory shaft 112 located on an eccentric axis 152 of the present invention in relation to the longitudinally axis 150 of the guide tube 108. The eccentrically mounted vibratory shaft 112 allows for the deployment of the cutter to a deployed position, as illustrated in FIG. 2B, upon rotation of the vibratory shaft 112. Upon extension of the cutter 114, as illustrated in FIG. 2B, the ultrasonic surgical cutting system can be rotated about the central axis of the guide tube such that the cutter 114 provides a circumferential groove in the surrounding bone 120.

The cutter 114 of the present invention can be deployed into an extended position via operation of a rotatable hand piece 116. In one embodiment, the rotatable hand piece 116 includes a geared mechanism in communication with the vibratory shaft 112 such that upon rotation of the rotatable hand piece 116 the cutter 114 is rotated along an eccentric axis 152 located parallel to the guide tube 108. Upon rotation of the vibratory shaft and the attached cutter 114, the cutter can be deployed a variety of levels of extension beyond the exterior wall of the guide tube 108, such that the cutter can cut a variety of depths in the surrounding bone or tissue. Following the deployment of the cutter 114, the entire ultrasonic surgical cutting system can be rotated, using the supplied rotatable hand piece 116 such that the cutter sweeps through a circumferential path. The circumferential sweep of the cutter 114 results in a circumferential cut in the surrounding bone or tissue with a width of cut corresponding to the width of the cutter 114 and a depth of cut related to the depth of the extended cutter beyond the exterior of the guide tube 108.

Using such an arrangement, cuts of varying depths in the surrounding bone or tissue can be made using an incremental approach. An initial cutter depth can be set and the ultrasonic surgical cutting system can revolved, thereby resulting in a first circumferential cut in the surrounding bone or tissue. The cutter 114 depth can then be increased, and the cutter swept through a second revolution, thereby creating a depth increase as compared to the initial cut in the surrounding bone or tissue. Using such an approach, one skilled in the art will readily recognize that deep cuts in the surrounding bone or tissue can be performed using a multi-pass arrangement such that cutter amplitude and frequency can be kept to a minimum, as a minimal amount of material are removed in each pass, thereby reducing heat buildup at the cutter 114. Such an arrangement offers the benefit of decreased potential for necrosis development in surrounding bone, as the cutter tip is maintained at a reduced temperature. In the alternative, one skilled in the art will recognize that a full depth cut can be performed in a single pass using the present invention in a situation where such a cut is surgically necessary and acceptable. In addition, in the alternative, the radius of the cut can be varied during the single pass to accommodate the shape of the pedicle region. Due to the oblong shape of the pedicle cross-section, the desire to control the cutting depth is optimal. As the axis of the vibratory shaft 112 is offset from the axis of the guide tube 108 the radius of the cut can be varied by simultaneously manipulating the extent of cutter extension beyond the guide tub 108 and the rotation of the ultrasonic cutting device. For example, the cutter extension can be infinitely varied as the ultrasonic cutting instrument is rotated along the central axis of the guide tube 108. Such an arrangement creates an infinite depth of cut up to the maximum extended length of the cutter 114.

When used in spinal stenosis correction surgery, for example, a circumferential cut originating from within a predefined hollow pathway region can be made at a fixed depth.

This circumferential cut through the pedicle region can be made in a single pass using a fully deployed lateral cutter, or can be made in several circumferential passes during which the cutter is deployed at an increasing depth along each pass. As the guide tube 108 is located within the predefined hollow pathway, the ultrasonic surgical cutter relationship is maintained throughout the cutting procedure such that a uniform cut results. Additionally, as the cutting originates from within the predefined hollow region, the cutting procedure remains minimally invasive.

The ultrasonic generator 100 provided a signal containing both a known amplitude and frequency. In one embodiment, a frequency of 22 kHz, and amplitude of 80 microns, can be utilized for ultrasonic cutting. As understood by one skilled in the art, both amplitude and frequency can be varied based upon the specific use of the ultrasonic surgical cutting system. For example, when used to cut bone, a low amplitude of the generated signal can be maintained such that excessive heating does not occur at cutter 114. Excessive heating at the cutter 144, when used in cutting bone, can result in bone necrosis. Additionally, using a low amplitude will reduce the likelihood of cutting soft tissue in which the cutter may come in contract once the outer edge of bone is reached. Employing a low amplitude signal therefore reduced excessive tip heating and the onset of necrosis. In the alternative, when the present ultrasonic surgical cutting system is employed to cut through soft tissue, the amplitude of the supplied signal can be increased such that the performance of the present invention when used to cut soft tissue is increased. For example, an increase in the speed of the blade, as governed by increases in the associated amplitude and frequency, offers increased ability to cut through soft tissue such as bone, while the cutter temperature remains reduced due to the cooling mechanism associated with the cutter. Employing a higher amplitude results in increased cutter 114 temperature, which serves to cauterize the region cut by the ultrasonic surgical cutting system, thereby preventing blood loss.

Figure 2C:
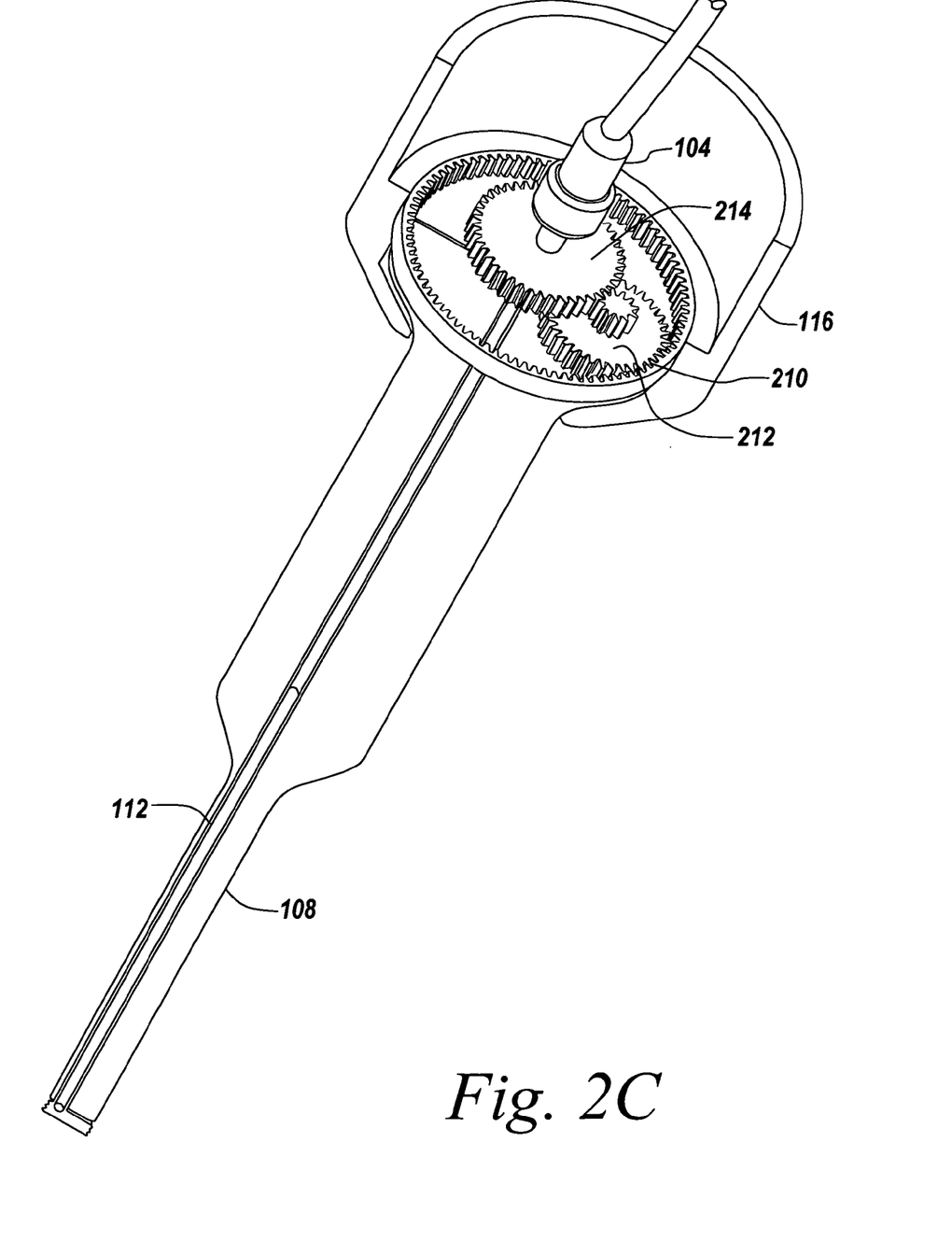
FIG. 2C is a detailed view of an illustrative embodiment of a portion of the system, wherein the internal workings of the rotatable hand piece are detailed.

FIG. 2C of the present invention is an illustrative cutaway example of the rotatable hand piece assembly 116 of the present invention. The rotatable hand piece assembly 116 performs the dual function of both extending the cutter 114 of FIG. 2B to a predetermined depth of cut beyond the confines of the external surface of the guide tube 108, as well as allowing a surgeon to rotate the entire ultrasonic surgical cutter system, such that the cutter 114 of FIG. 2B sweeps through an intended range of motion. The movement of the cutter 114 of FIG. 2B thereby creates a circumferential groove in the surrounding bone or tissue in contact with the cutter. For illustrative purposes, cutter is herein described in relation to a full circular sweep, yet one skilled in the art will readily recognize that the cutter can be swept through an isolated range of motion. In light of this, detailed removal of regions of bone can be effectuated using the present invention. As illustrated in FIG. 2C, the transducer 104 and associated vibratory shaft 112 are located in an offset manner in relation to the centerline 150 of the rotatable hand piece 16 and guide tube 108 such that the cutter 114 of FIG. 2B maintains an eccentric range of motion when moved from the retracted position within the guide tube to the extended position. Furthermore, in the illustrative embodiment, the rotatable hand piece 116 includes a geared mechanism for deploying the cutter from the stowed position. As illustrated in the present embodiment the geared mechanism 200 includes a ring gear 210 associated with the rotatable hand piece. This ring gear, upon rotation of the rotatable hand piece, provides for transmission of rotational energy to an intermediate spur gear 212. The intermediate spur gear 212 further transfer the initial rotation of the rotatable hand piece 116 to a pinion gear 214 associated with the vibratory shaft. Such a transfer of rotational energy results in the rotation of the vibratory shaft 112 and the subsequent deployment of the attached cutter 114. One skilled in the art will readily recognize that the sizing and tooth count of the illustrated gears can be sized and specified such that the requisite mechanical advantage and rotational speeds are provided in accordance with the needs of the present invention.

The geared mechanism 200 of the present embodiment is used solely for illustrative purpose. One skilled in the art will readily recognize that the geared mechanism 200 may be replaced by numerous alternative mechanisms capable of extending the cutter 114. For example, a rack and pinion arrangement can be utilized in place of the circular gear train of the present embodiment. In the alternative, a planetary gear arrangement can be utilized for use in extending the cutter 114 and providing for a means by which the ultrasonic surgical cutting system can be rotated along the longitudinal axis of the guide tube 108.

Furthermore, upon deploying the cutter 114 of FIG. 2B, the rotatable hand piece 116 is further rotated such that the entire ultrasonic surgical cutting system is rotated about the longitudinal axis (not shown) of the guide tube 108. Rotation of the ultrasonic surgical cutting system, and eccentric mounted vibratory shaft 112 and attached cutter 114, results in the removal of material from the surrounding hollow pathway 122. A full rotation of the rotatable hand piece 116 thereby results in a circular groove in the material surrounding the hollow pathway 122. Additionally, the cutter 114 depth can be gradually advanced such that that a deepening circular groove can be traced following several rotations of the rotatable hand piece 116.

Figure 3A:
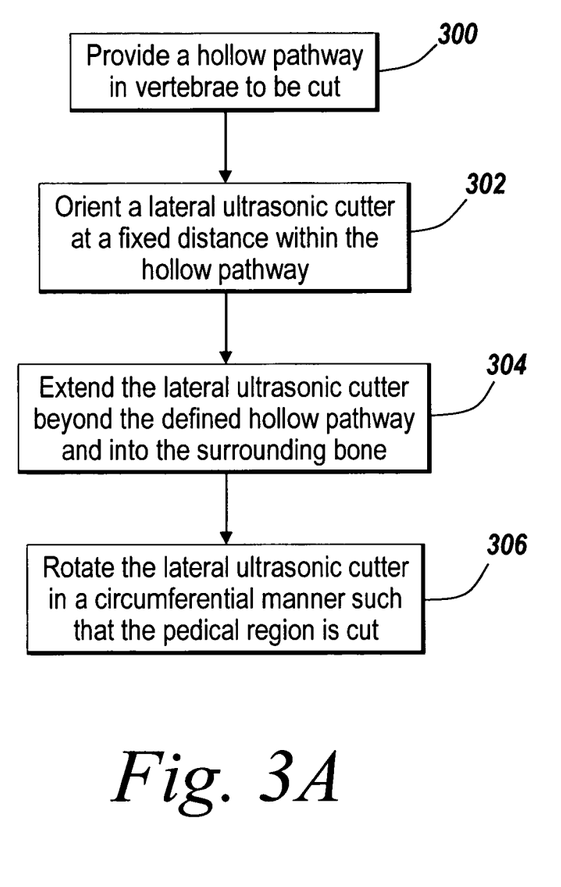
FIG. 3A is a flowchart illustrating the steps required in spinal stenosis correction when the pedicle region of a vertebrae is cut.

FIG. 3A is a flowchart illustrating the steps necessary in using the present invention to correct stenosis by cutting a pedicle region of a vertebrae. In accordance with step 300 a hollow pathway is initially provided in a pedicle region of the vertebrae to be cut. This hollow pathway can be provided using numerous existing techniques, as understood by one skilled din the art. For example, a drilling mechanism can be used such that a circular hole is bored into the intended region to be cut. In accordance with step 302, a lateral ultrasonic cutter is oriented within the hollow pathway at a fixed distance such that the cutter is appropriately located for cutting of the pedicle region of a vertebrae. The lateral ultrasonic cutter is then extended (304) beyond the hollow region of the hollow pathway and into the surrounding bone of the vertebrae. Following the extension of the lateral ultrasonic cutter, the cutter is rotated in a circumferential manner such that a circumferential groove is cut within the surrounding bone of the hollow pathway. (step 306) The ultrasonic lateral cutter may cut through the pedicle region in a single pass, or the depth of cut may be incrementally increased such that the ultrasonic lateral cutter cuts through the pedicle region in multiple revolutions.

Figure 3B:
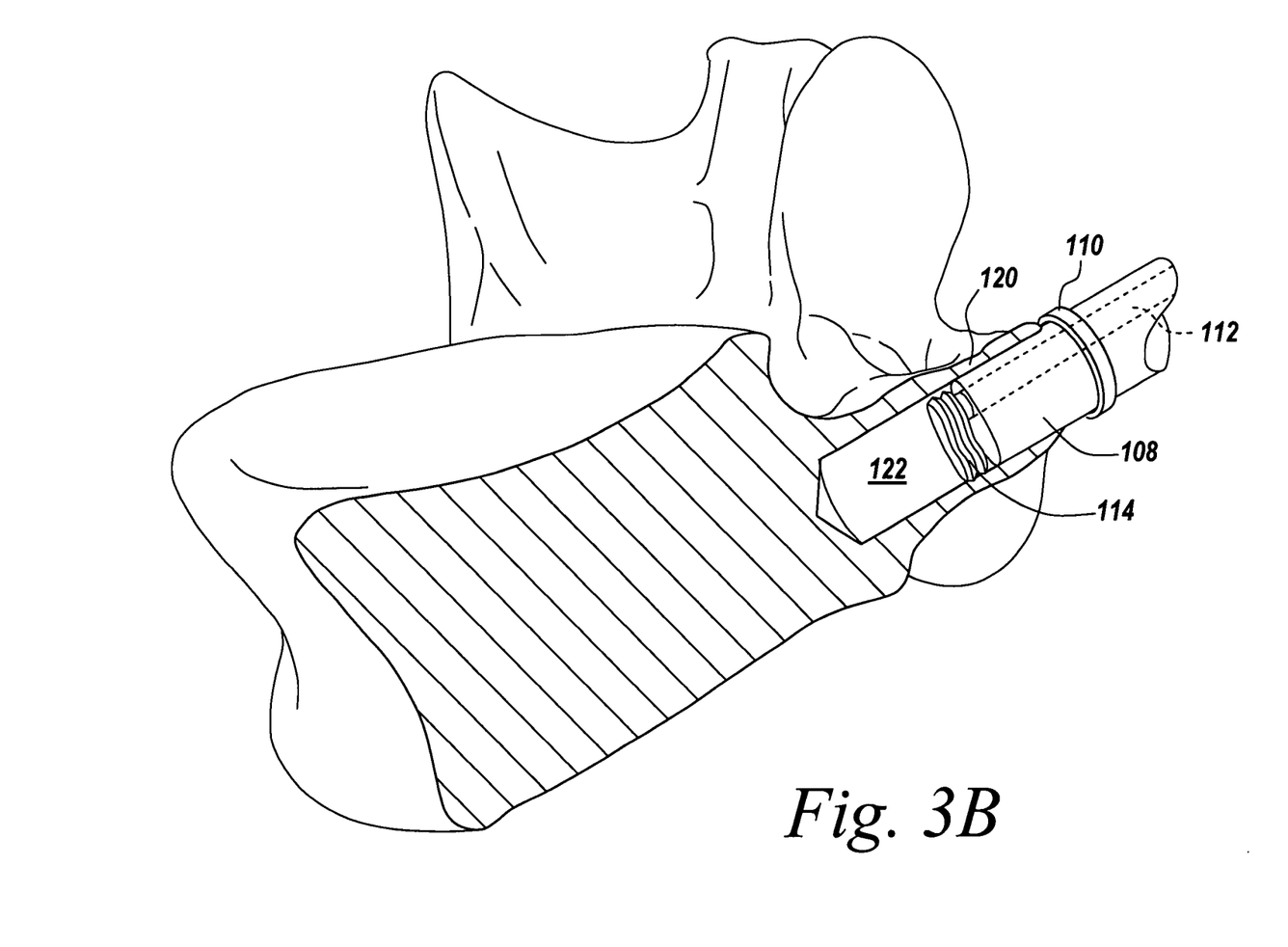
FIG. 3B is an illustrative graphical embodiment of the present invention when used in stenosis correction surgery within a vertebrae of a patient.

FIG. 3B illustrates an embodiment of the present invention when used in stenosis correction in a lower vertebrae of a human patient. The lower vertebra is provided with a hollow pathway 122 which can be drilled using existing bone drilling techniques. Following the provision of the hollow pathway, the guide tube, and associated cutter 114 can be inserted into the hollow pathway 122 using the surrounding bone 120 as a guide to locate the guide tube 108 against. The guide tube 108 can be deployed to a fixed distance either manually, or can be placed within the hollow pathway 122 until the adjustable stop 110 comes in contact with the upper region of the hollow pathway 122. Following insertion of the guide tube within the hollow pathway 122, the presently retracted cutter 114 can be deployed upon rotation of the eccentrically mounted vibratory shaft 112. Rotation of the vibratory shaft 112 occurs following rotation of the hand piece assembly 116 of FIG. 2C. Due to the eccentric location of the vibratory shaft 112, when viewed relative to the guide tube 108 centerline, the cutter 114 is deployed in a manner where the cutter extends beyond the confines of the guide tube 108. Using such an arrangement, the cutter, which is receiving an ultrasonic vibration comprising an amplitude and frequency, can be rotated in a circumferential manner, thereby producing a groove in the surrounding bone 120. One skilled in the art will readily recognize that the present cutter 114 is oriented perpendicular to the vibratory shaft 112 but any number of relative angles between cutter 114 and vibratory shaft 112 can be employed.

Figure 4:
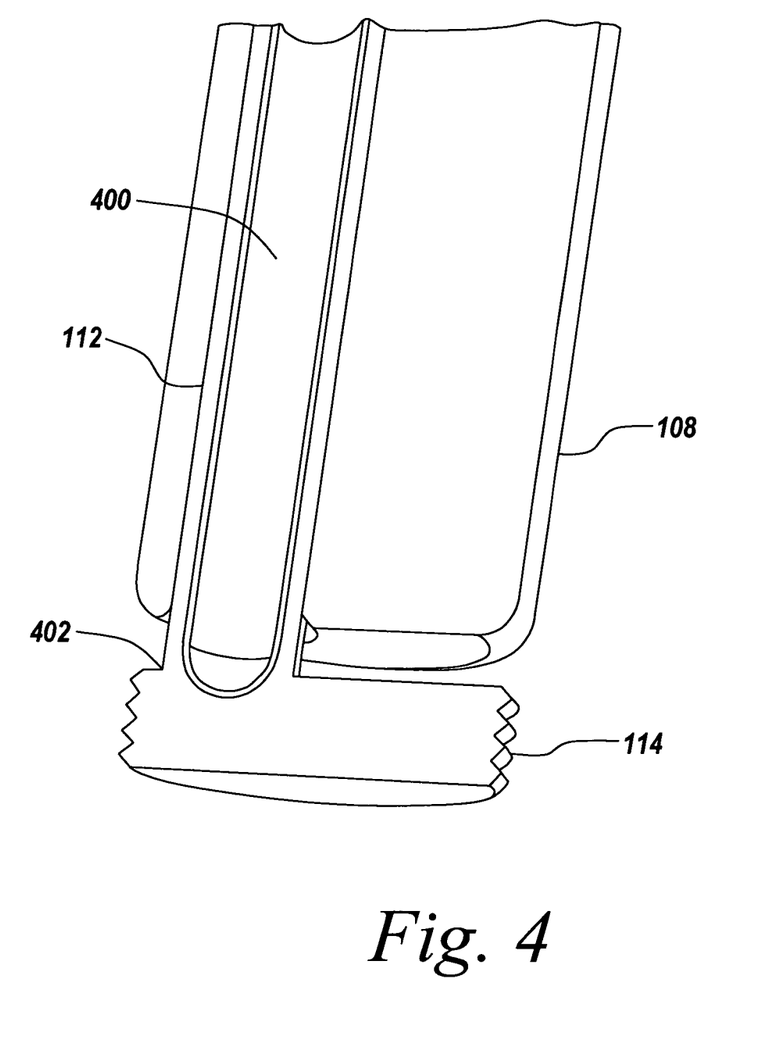
FIG. 4 is a cutaway view of the lateral cutter of the present invention when disposed upon a hollow vibratory shaft for use in convective cooling of the lateral cutter.

FIG. 4 of the present invention illustrated the use of a convective cooling mechanism for use with the present invention. The convective cooling pathway 400 is located internal to the vibratory shaft 112 and extend along the vibratory shaft 112 for a sufficient distance to adequately cool the cutter 114 associated with the vibratory shaft 112. As the cutter 114 of the present invention is in thermal contact with the vibratory shaft 112 of the present embodiment, heat generated in the cutter during operation is passed to the vibratory shaft through conduction. Heat passed to the distal end of the vibratory shaft adjacent to the cutter 114 is then passed to the convective cooling pathway 400 located internal to the vibratory shaft 112. Within the convective cooling pathway 400 a thermal gradient is established such that a working fluid is circulate along the thermal gradient from the cutter region 114 to the opposing end of the convective cooling pathway.

In one embodiment the convective cooling pathway includes a cellular matrix arrangement disposed within the convective cooling pathway 400. Existing conductive cooling pathways for use in surgical forceps are recognizable by one skilled in the art. One such example of convective cooling pathways is exhibited in the IsoCool™ Bipolar Forceps, herein incorporated by reference, offered by Codman, a Johnson & Johnson Company. The cellular matrix has a hollow central region parallel to the centerline of the vibratory shaft 112 such that a heated working fluid may travel up the hollow central region. In operation, the working fluid is instantly evaporated at the interface between vibratory shaft 112 and cutter 114. This now gaseous working fluid travels up the hollow central region of the convective cooling pathway 400 wherein it slowly cools as if moves further from the heated vibratory shaft 112 cutter 114 interface. The working fluid may then return to the interface 402 by passing through the cellular matrix of the convective cooling pathway. In one embodiment the cellular matrix may be made of a copper compound. In the present embodiment, the movement of the working fluid within the convective cooling pathway 400 is driven by the associated thermal gradient provided between the heated interface 402 region and the cool opposing end of the conductive cooling pathway 400. Those skilled in the art will readily recognize that the described cellular matrix arrangement is solely used for illustrative purposes and may be substituted by numerous convective cooling mechanisms as understood by one skilled in the art.

The use of the convective cooling pathway 400 with the present invention allows for the cooling of the cutter 114 such that heat generated at the cutter during use is partially or fully removed. In light of this, the cooled cutter 114 therefore reduces inherent problems with bone necrosis or inadvertent damage to soft tissue in regions surrounding the cutter 114. Furthermore, should the present invention be used in the cutting of soft tissue, the use of a cooled cutter prevents the inherent problems with tissue sticking to the cutter due to the high temperature associated with existing cutters.

FIGS. 1 through 4, wherein like parts are designated by like reference numerals throughout, illustrate an example embodiment of an ultrasonic cutting device according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

Having described the invention, what is claimed as new and desired to be secured by Letters Patent is:

1. A method for cutting the pedicle region of a vertebra during spinal surgery with an ultrasonic cutting tool, comprising:
  providing a pathway into the pedicle of vertebrae to be cut;
  locating an ultrasonic cutting tool into said pathway at a fixed distance, wherein said tool contains
    an ultrasonic transducer element for producing an ultrasonic output;
    a rotatable handpiece sized and oriented to contain the ultrasonic transducer;
    a lateral cutting tip associated with the ultrasonic transducer element, wherein the lateral cutting tip oriented perpendicular to the ultrasonic transducer; and
    a geared mechanism for rotating said lateral cutting mechanism in response to rotation of the rotatable handpiece relative to the ultrasonic cutting tool;
    a convective cooling pathway associated with the lateral cutting tip;
  rotating said lateral cutting tip in a circumferential manner about an eccentric axis of the ultrasonic cutting tool by rotating the rotatable handpiece to engage the geared mechanism to extend said lateral cutting tip from within said pathway to a predetermined position, the eccentric axis being a center of rotation of the lateral cutting tip and parallel to a longitudinal axis of the ultrasonic cutting tool; and
  at the predetermined position, rotating said lateral cutting tip about the longitudinal axis of the ultrasonic cutting tool by rotating the rotatable handpiece and thus rotating the ultrasonic cutting tool with the lateral cutting tip extended to form a circumferential groove in the surrounding pedicle of the pathway, wherein heat generated by the lateral cutting tip is removed using the convective cooling pathway.

2. The method of claim 1, wherein said cutting tip is constructed of a biocompatible material.

3. The method of claim 1, wherein said ultrasonic cutting tool operates in the frequency range between about 22 Khz and about 45 Khz.

4. The method of claim 1, wherein said ultrasonic cutting tool operates in the amplitude range between about 50 to about 100 microns.

5. The method of claim 1, further comprising the providing of a guide tube, wherein said guide tube is sized and oriented to fit within the hollow pathway into the vertebrae.

6. The method of claim 5, further comprising the providing of an adjustable stop, wherein said adjustable stop is associated with the guide tube such that the distance that the guide tube is inserted into the hollow pathway is predefined.

7. A method of performing a surgical procedure comprising:

delivering a lateral cutting tip of an ultrasonic cutting tool to proximate a vertebra, wherein the lateral cutting tip is oriented perpendicular to the ultrasonic cutting tool;

cutting a portion of the vertebra with the lateral cutting tip of the ultrasonic cutting tool, the step of cutting comprising rotating the lateral cutting tip about an eccentric axis of the ultrasonic cutting tool by rotating a rotatable handpiece relative to the ultrasonic cutting tool to engage a geared mechanism in the ultrasonic cutting tool to extend said lateral cutting tip to a predetermined position, the eccentric axis being a center of rotation of the lateral cutting tip and parallel to a longitudinal axis of the ultrasonic cutting tool, and at the predetermined position, rotating said lateral cutting tip about the longitudinal axis of the ultrasonic cutting tool by rotating the rotatable handpiece and thus rotating the ultrasonic cutting tool with the lateral cutting tip extended to form a circumferential groove in the vertebrae; and cooling the cutting tip to temperature sufficient to inhibit necrosis of tissue proximate the cutting tip using a convection cooling system coupled to the ultrasonic cutting tool.

8. The method of 7, wherein the cutting tip is cooled to a temperature less than approximately 50° C.

9. The method of 7, wherein the cutting tip is cooled to a temperature less than approximately 45° C.

10. The method of 7, wherein the cutting tip is cooled to a temperature less than approximately 40° C.

11. The method of 7, wherein the cutting tip is cooled to a temperature approximate to body temperature.

\* \* \* \* \*